US011116764B2

(12) United States Patent
Nirogi et al.

(10) Patent No.: US 11,116,764 B2
(45) Date of Patent: Sep. 14, 2021

(54) COMBINATION OF PURE 5-HT6 RECEPTOR ANTAGONISTS WITH NMDA RECEPTOR ANTAGONIST

(71) Applicant: SUVEN LIFE SCIENCES LIMITED, Telangana (IN)

(72) Inventors: Ramakrishna Nirogi, Telangana (IN); Anil Karbhari Shinde, Telangana (IN); Pradeep Jayarajan, Telangana (IN); Gopinadh Bhyrapuneni, Telangana (IN); Ramasastri Kambhampati, Telangana (IN); Venkateswarlu Jasti, Telangana (IN)

(73) Assignee: Suven Life Sciences Limited, Hyderabad (IN)

( * ) Notice: Subject to any disclaimer, the term of this patent is extended or adjusted under 35 U.S.C. 154(b) by 279 days.

(21) Appl. No.: 16/097,458

(22) PCT Filed: Aug. 3, 2016

(86) PCT No.: PCT/IB2016/054674
§ 371 (c)(1),
(2) Date: Oct. 29, 2018

(87) PCT Pub. No.: WO2017/199072
PCT Pub. Date: Nov. 23, 2017

(65) Prior Publication Data
US 2019/0175586 A1    Jun. 13, 2019

(30) Foreign Application Priority Data

May 18, 2016  (IN) .............................. 201641017203

(51) Int. Cl.
*A61K 31/496*    (2006.01)
*A61K 31/13*    (2006.01)

(52) U.S. Cl.
CPC ............ *A61K 31/496* (2013.01); *A61K 31/13* (2013.01)

(58) Field of Classification Search
CPC .. A61K 2300/00; A61K 31/496; A61K 31/13; A61K 31/445; A61K 31/31; A61K 31/538; A61K 31/4468; A61K 31/4709; A61K 31/4725; A61K 31/24; A61K 31/473; A61K 31/55; A61P 25/28; A61P 25/18; A61P 25/00; A61P 25/16; A61P 43/00; A61P 25/22; A61P 25/24; A61P 25/08; A61P 1/00; A61P 3/04; A61P 1/04; A61P 25/06; A61P 25/20; A61P 25/30; A61P 29/00; A61P 9/00; A61P 25/14; C07D 209/08; C07D 209/30; C07D 211/58; C07D 295/30; C07D 333/62; C07D 401/12; C07D 401/14; C07D 413/04

See application file for complete search history.

(56) References Cited

U.S. PATENT DOCUMENTS

| 7,875,605 B2 * | 1/2011 | Ramakrishna .......... A61P 19/00 514/211.08 |
| 2010/0074955 A1 * | 3/2010 | Buschmann .............. A61P 1/10 424/485 |

FOREIGN PATENT DOCUMENTS

| EP | 1902733 | 3/2008 |
| WO | 2004/048330 | 6/2004 |
| WO | 2015/083179 | 6/2015 |

OTHER PUBLICATIONS

Namenda (https://www.accessdata.fda.gov/drugsatfda_docs/label/2013/021487s010s012s014,021627s008lbl.pdf, 2013). (Year: 2013).*
Jayarajan et al., "5-HT6 Antagonist SUVN-502 Potentiates the Procognitive and Neurochemical Effects of Donepezil and Memantine" Alzheimer's and Dementia: The Journal of the Alzheimer's Association 11(7):P472 (2015) XP029353767 P1-302.
Abraham et al., "Role of Glutamate and Advantages of Combining Memantine With a 5TH6 Ligand in a Model of Depression" Pharmacological Reports 66(3):394-398 (2014).
Nirogi et al., "SUVN-502: A Potent and Selective 5-HT6 Antagonist, Potential Drug for the Treatment of Alzheimer'S Disease" Alzheimer's and Dementia: The Journal of the Alzheimer's Association 7(4):S659 (Jul. 1, 2011) XP055335504 P3-451.
Dawson et al., "In vivo effects of the 5-HT6 antagonist SB-271046 on striatal and frontal cortex extracellular concentrations of noradrenaline, dopamine, 5-HT, glutamate and aspartate" British Journal of Pharmacology 130:23-26 (2000).
Areosa Sastre et al., "Memantine for dementia (Review)" Cochrane Library, Cochrane Database of Systematic Reviews 4:1-46 (2004).
Schneider et al., "Lack of Evidence for the Efficacy of Memantine in Mild Alzheimer Disease" Arch Neurol.68(8):991-998 (2011).
Monsma et al., "Cloning and Expression of a Novel Serotonin Receptor with High Affinity for Tricyclic Psychotropic Drugs" Amer. Soc. for Pharmacol. and Exper. Therapeut., Molecular Pharmacol. 43:320-327 (1993).
Bentley et al., "Investigation of stretching behaviour induced by the selective 5-HT6 receptor antagonist, Ro 04/6790, in rats" Br J. Pharmacol. 126:1537-1542 (1999).
Noolley et al., "5-ht6 Receptors" Current Drug Targets—CNS & Neurological Disorders 3:59-79 (2004).
Kohen et al., "Cloning of the mouse 5-HT6 serotonin receptor and mutagenesis studies of the third cytoplasmic loop" Molec. Brain Res. 90:110-117 (2001).
Romero et al., "Efficacy of selective 5-HT6 receptor ligands determined by monitoring 5-HT6 receptor-mediated cAMP signaling pathways" British J. Pharmacol. 148:1133-1143 (2006).

(Continued)

*Primary Examiner* — Umamaheswari Ramachandran
(74) *Attorney, Agent, or Firm* — IpHorgan Ltd.

(57) ABSTRACT

The present invention relates to pure 5-HT6 receptor antagonist or the pharmaceutically acceptable salt(s) thereof in combination with or as adjunct to NMDA receptor antagonist and their use in the treatment of cognitive disorders. The invention further relates to the pharmaceutical composition containing the said combination.

24 Claims, 4 Drawing Sheets

(56) References Cited

OTHER PUBLICATIONS

Figure 1A:
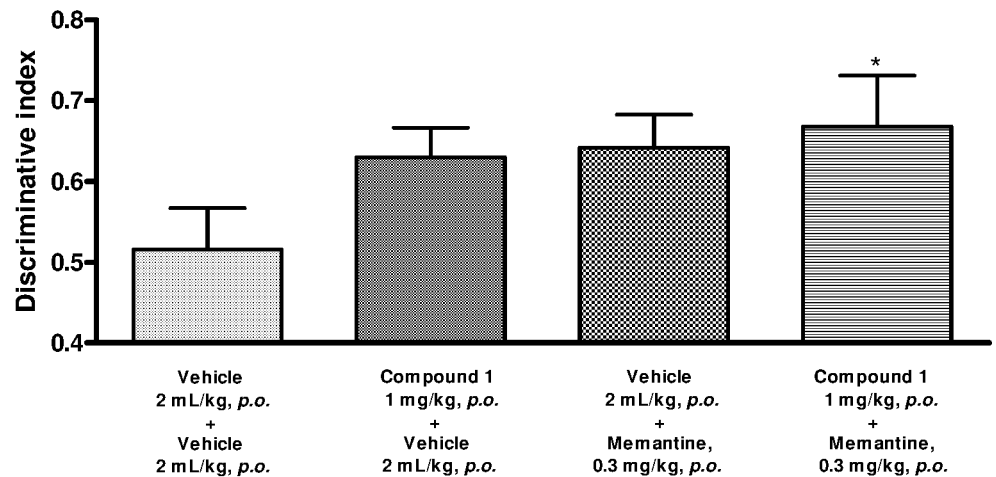

Ennaceur et al., "A new one-trial test for neurobiological studies of memory in rats. 1: Behavioral data" Behavioural Brain Research 31:47-59(1988).
European Patent Office, "International Search Report" and "Written Opinion" dated Feb. 1, 2017 in PCT/IB2016/054674.
European Patent Office, "International Preliminary Report on Patentability" completed Aug. 2, 2018 in PCT/IB2016/054674.

* cited by examiner

Data represents Mean ± SEM of discriminative index. *$p<0.05$ Vs vehicle (Kruskal-Wallis followed by Dunn's Multiple Comparison Test) N=8-11

Data represents Mean ± SEM of discriminative index. *$p<0.05$ Vs vehicle (Kruskal-Wallis followed by Dunn's Multiple Comparison Test) N=6-11

Data represents Mean ± SEM of discriminative index. *p<0.05 Vs vehicle (Kruskal-Wallis followed by Dunn's Multiple Comparison Test) N=9-11

(a)

(b)

(a) Data expressed as Mean ± SEM. *$p<0.05$, $p<0.01$ Vs memantine alone (Bonferroni post test) (b) Area under the curve value ± SEM. $p<0.01$ Vs memantine alone (Unpaired t test)

(a)

(b)

(a) Percent change from mean basal levels expressed as Mean ± SEM. *$p<0.05$ Vs memantine alone (Bonferroni posttest). (b) Cumulative changes in acetylcholine levels expressed as mean area under the curve (AUC) ± S.E.M. *$p<0.05$ (Dunnett's Multiple Comparison Test).

COMBINATION OF PURE 5-HT6 RECEPTOR ANTAGONISTS WITH NMDA RECEPTOR ANTAGONIST

CROSS REFERENCE TO RELATED APPLICATIONS

This application is a national stage completion application of PCT Application No. PCT/IB2016/054674, filed Aug. 3, 2016, and claims the benefit of India Application No. 201641017203, filed May 18, 2016. Each of these applications is incorporated by reference herein in its entirety.

FIELD OF THE INVENTION

The present invention relates to pure $5$-$HT_6$ receptor ($5$-$HT_6R$) antagonists, or the pharmaceutically acceptable salt(s) in combination with or as adjunct to N-Methyl-D-aspartate (NMDA) receptor antagonist and their use in the treatment of cognitive disorders. The invention further relates to the pharmaceutical composition containing the said combination.

BACKGROUND OF INVENTION

Alzheimer's disease (AD) is the most common cause of dementia worldwide. The exponential rise in the number of cases of AD in the past and the future projection over the next few decades is anticipated to result in great pressure on the social and health-care systems of developed and developing economies alike. AD also imposes tremendous emotional and financial burden to the patient's family and community.

It is known that glutamate neurons have synaptic connections on cholinergic neurons in brain areas associated with learning and memory. Blockade of glutamatergic NMDA receptors stimulate the synaptic release of acetylcholine. Antagonists of $5$-$HT_6$ receptor also elevate glutamatergic neurotransmission {*British Journal of Pharmacology*, 2000, 130, 23-26), which is important for long-term potentiation, learning, and memory. The current treatment options rely on treatment of cognitive manifestations of AD through NMDA receptor inhibitors. Memantine, a NMDA receptor antagonist was moderately efficacious in the treatment of moderate to severe Alzheimer's disease. Its effect in the initial stages of AD are unknown {*The Cochrane Library*, 2004, 4, 1-46) and does not alter the cognitive ability or delay the onset of AD {*Archives of Neurology*, 2011, 68(8), 991-998).

5-Hydroxytryptamine 6 receptor ($5$-$HT_6R$), a member of GPCR family is exclusively expressed in the brain, particularly in areas associated with cognition, such as the hippocampus and frontal cortex (*Molecular Pharmacology*, 1993, 43, 320-327). Activation of the $5$-$HT_6R$ usually represses cholinergic function (*British Journal of Pharmacology*, 1999, 126, 1537-1542), whereas blockade of the receptor improves the cognitive functions. Thus, $5$-$HT_6R$ may be a viable target for pharmacologic intervention to improve the cognitive function of patients with AD. As $5$-$HT_6R$ is exclusively located centrally, it is believed that $5$-$HT_6R$ antagonists would have limited peripheral side effects, including the ones which are commonly associated with cholinesterase inhibitors. Antagonism of this receptor by several investigational compounds has been shown to improve learning and memory in animal models (*CNS & Neurological Disorders—Drug Targets*, 2004, 3, 59-79).

The $5$-$HT_6R$ antagonists have been shown to increase extracellular glutamate levels in addition to acetylcholine. It is, thus, possible that the cognitive effects of $5$-$HT_6R$ antagonists and other treatments for cognitive disorders could be the result of interactions with both cholinergic and glutamatergic systems involved in learning and memory.

Memantine is another approved treatment for AD, which acts on the glutamatergic system by inhibiting NMDA receptors under conditions of excess stimulation. It may act to protect glutamate neurons from excessive glutamate stimulation.

The compounds of the present invention are pure $5$-$HT_6R$ antagonists with high affinity and very high selectivity over closely related serotonin receptor subtypes and improve learning and memory in animals. The $5$-$HT_6R$ antagonist compounds mentioned here are described in U.S. Pat. No. 7,875,605 which is incorporated by reference. The preparation of these compounds is given in the said patent.

The patent application WO2008034815A1 discloses the combination of memantine, an NMDA receptor ligand and a compound with $5$-$HT_6R$ affinity and their use in the treatment of cognitive disorders.

As the treatment of AD is chronic in nature, there is a desperate unmet medical need for better and safer treatment options. A therapeutic strategy eagerly sought for AD patients is to target an improvement with an adjunct to existing therapies that would bring additional relief for patients, lower the burden on the caregiver and allow the patient to enjoy a better quality of life without the need for institutional care and/or hospitalization.

The instant invention provides pure $5$-$HT_6R$ antagonists or the pharmaceutically acceptable salt(s) thereof, which enhances the cognitive function of patients on treatment in combination with NMDA receptor antagonist. The present invention is based on the unusual finding that the combination of compounds with pure $5$-$HT_6R$ antagonistic activity and the compounds which act as NMDA receptor antagonists (for example memantine) demonstrate synergistic effect in their pharmacological activity. Memantine acts by blocking the glutamatergic neurotransmissions in the brain. The $5$-$HT_6R$ antagonists have been shown to increase extracellular glutamate levels in addition to acetylcholine. Hence it is not anticipated that the combination of a pure $5$-$HT_6R$ antagonist+memantine would result in synergistic procognitive effects. However surprisingly, the combination of pure $5$-$HT_6R$ antagonists+NMDA receptor antagonist showed synergistic effects in animal models and also increased the levels of acetylcholine, a neurotransmitter that plays a vital role in cognitive improvement. Based on these results one can infer that such combined administration and/or co-treatment of pure $5$-$HT_6R$ antagonist+NMDA receptor antagonist, may result in beneficial effect to improve the therapeutic efficacy in humans. Further the pure $5$-$HT_6R$ antagonists or the pharmaceutically acceptable salt(s) thereof of the instant invention enhances the effect of the NMDA receptor antagonist in the treatment of cognitive disorders.

SUMMARY OF THE INVENTION

The object of the present invention is to provide an improved combination therapy for the treatment of cognitive disorders, such as Alzheimer's disease, schizophrenia, Parkinson's disease, lewy body dementia, vascular dementia or frontotemporal dementia.

In the first aspect, the present invention relates to combination of pure $5$-$HT_6$ receptor antagonist and NMDA receptor antagonist; wherein the pure $5$-$HT_6$ receptor antagonist is selected from:

1-[(2-Bromophenyl) sulfonyl]-5-methoxy-3-[(4-methyl-1-piperazinyl)methyl]-1H-indole;
1-[(4-Fluorophenyl) sulfonyl]-5-methoxy-3-[(4-methyl-1-piperazinyl)methyl]-1H-indole; and
1-[(4-Isopropylphenyl)sulfonyl]-5-methoxy-3-[(4-methyl-1-piperazinyl)methyl]-1H-indole; or a pharmaceutically acceptable salt thereof.

In another aspect, the present invention relates to combination of pure $5\text{-}HT_6$ receptor antagonist and NMDA receptor antagonist; wherein the pure $5\text{-}HT_6$ receptor antagonist is 1-[(2-Bromophenyl)sulfonyl]-5-methoxy-3-[(4-methyl-1-piperazinyl)methyl]-1H-indole or a pharmaceutically acceptable salt thereof.

In another aspect, the present invention relates to combination of pure $5\text{-}HT_6$ receptor antagonist and NMDA receptor antagonist; wherein the pure $5\text{-}HT_6$ receptor antagonist is 1-[(4-Fluorophenyl)sulfonyl]-5-methoxy-3-[(4-methyl-1-piperazinyl)methyl]-1H-indole or a pharmaceutically acceptable salt thereof.

In another aspect, the present invention relates to combination of pure $5\text{-}HT_6$ receptor antagonist and NMDA receptor antagonist; wherein the pure $5\text{-}HT_6$ receptor antagonist is 1-[(4-Isopropylphenyl) sulfonyl]-5-methoxy-3-[(4-methyl-1piperazinyl)methyl]-1H-indole or a pharmaceutically acceptable salt thereof.

In another aspect, the present invention relates to combination of pure $5\text{-}HT_6$ receptor antagonist and NMDA receptor antagonist; wherein the NMDA receptor antagonist is memantine or a pharmaceutically acceptable salt thereof.

In yet another aspect, the present invention relates to combination of 1-[(2-Bromophenyl)sulfonyl]-5-methoxy-3-[(4-methyl-1-piperazinyl)methyl]-1H-indole or a pharmaceutically acceptable salt thereof and memantine or a pharmaceutically acceptable salt thereof.

In yet another aspect, the present invention relates to combination of 1-[(2-Bromophenyl) sulfonyl]-5-methoxy-3-[(4-methyl-1-piperazinyl)methyl]-1H-indole dimesylate monohydrate and memantine hydrochloride.

In yet another aspect, the present invention relates to the said combination for use in the treatment of cognitive disorders such as Alzheimer's disease, schizophrenia, Parkinson's disease, lewy body dementia, vascular dementia or frontotemporal dementia.

In yet another aspect, the present invention relates to method of treatment of cognitive disorders such as Alzheimer's disease, schizophrenia, Parkinson's disease, lewy body dementia, vascular dementia or frontotemporal dementia comprising administering to a patient in need thereof a therapeutically effective amount of the said combination.

In yet another aspect, the present invention relates to the said combination in the manufacture of medicament for the treatment of cognitive disorders such as Alzheimer's disease, schizophrenia, Parkinson's disease, lewy body dementia, vascular dementia or frontotemporal dementia.

In yet another aspect, the present invention relates to 1-[(2-Bromophenyl)sulfonyl]-5-methoxy-3-[(4-methyl-1-piperazinyl)methyl]-1H-indole or a pharmaceutically acceptable salt thereof for use in the adjunct treatment of cognitive disorders such as Alzheimer's disease, schizophrenia, Parkinson's disease, lewy body dementia, vascular dementia or frontotemporal dementia in a patient on treatment with NMDA receptor antagonist or a pharmaceutically acceptable salt thereof.

In yet another aspect, the present invention relates to 1-[(4-Fluorophenyl)sulfonyl]-5-methoxy-3-[(4-methyl-1-piperazinyl)methyl]-1H-indole or a pharmaceutically acceptable salt thereof for use in the adjunct treatment of cognitive disorders such as Alzheimer's disease, schizophrenia, Parkinson's disease, lewy body dementia, vascular dementia, or frontotemporal dementia in a patient on treatment with NMDA receptor antagonist or a pharmaceutically acceptable salt thereof.

In yet another aspect, the present invention relates to 1-[(4-Isopropylphenyl) sulfonyl]-5-methoxy-3-[(4-methyl-1-piperazinyl)methyl]-1H-indole or a pharmaceutically acceptable salt thereof for use in the adjunct treatment of cognitive disorders such as Alzheimer's disease, schizophrenia, Parkinson's disease, lewy body dementia, vascular dementia or frontotemporal dementia in a patient on treatment with NMDA receptor antagonist or a pharmaceutically acceptable salt thereof.

In yet another aspect, the present invention relates to 1-[(2-Bromophenyl)sulfonyl]-5-methoxy-3-[(4-methyl-1-piperazinyl)methyl]-1H-indole or a pharmaceutically acceptable salt thereof for use in combination with or adjunct to NMDA receptor antagonist or a pharmaceutically acceptable salt thereof for the treatment of cognitive disorders such as Alzheimer's disease, schizophrenia, Parkinson's disease, lewy body dementia, vascular dementia or frontotemporal dementia.

In another aspect, the present invention relates to method of treatment of cognitive disorders comprising administering to a patient in need thereof a therapeutically effective amount of 1-[(2-Bromophenyl)sulfonyl]-5-methoxy-3-[(4-methyl-1-piperazinyl)methyl]-1H-indole or a pharmaceutically acceptable salt thereof in combination with or as an adjunct to memantine or a pharmaceutically acceptable salt thereof.

In yet another aspect, the present invention relates to use of a combination of 1-[(2-Bromophenyl) sulfonyl]-5-methoxy-3-[(4-methyl-1-piperazinyl)methyl]-1H-indole or a pharmaceutically acceptable salt thereof and memantine or a pharmaceutically acceptable salt thereof for the treatment of cognitive disorders such as Alzheimer's disease, schizophrenia, Parkinson's disease, lewy body dementia, vascular dementia or frontotemporal dementia.

In another aspect, the present invention relates to pharmaceutical composition comprising the said combination and a pharmaceutically acceptable excipients or combination thereof.

In another aspect, the present invention relates to pharmaceutical composition comprising 1-[(2-Bromophenyl) sulfonyl]-5-methoxy-3-[(4-methyl-1-piperazinyl)methyl]-1H-indole or a pharmaceutically acceptable salt thereof and memantine or a pharmaceutically acceptable salt thereof and pharmaceutically acceptable excipients or combination thereof for use in the treatment of cognitive disorders such as Alzheimer's disease, schizophrenia, Parkinson's disease, lewy body dementia, vascular dementia or frontotemporal dementia.

BRIEF DESCRIPTION OF THE DIAGRAMS

Figure 1B:
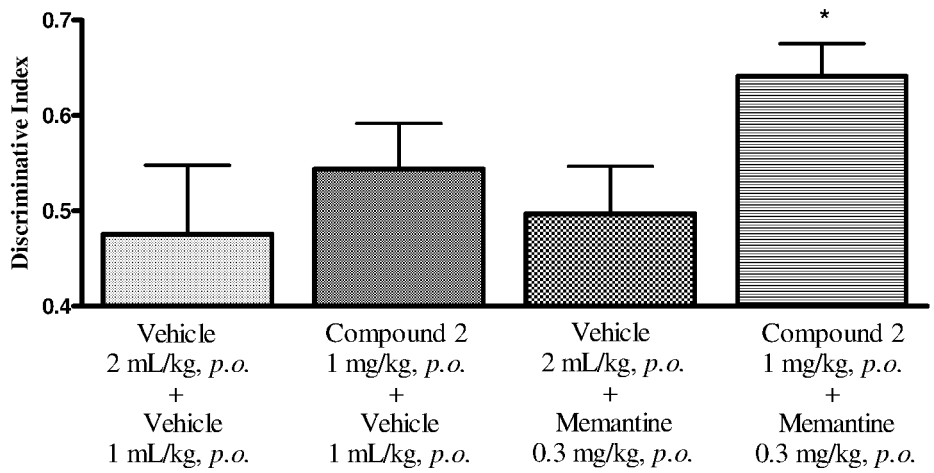
Figure 1C:
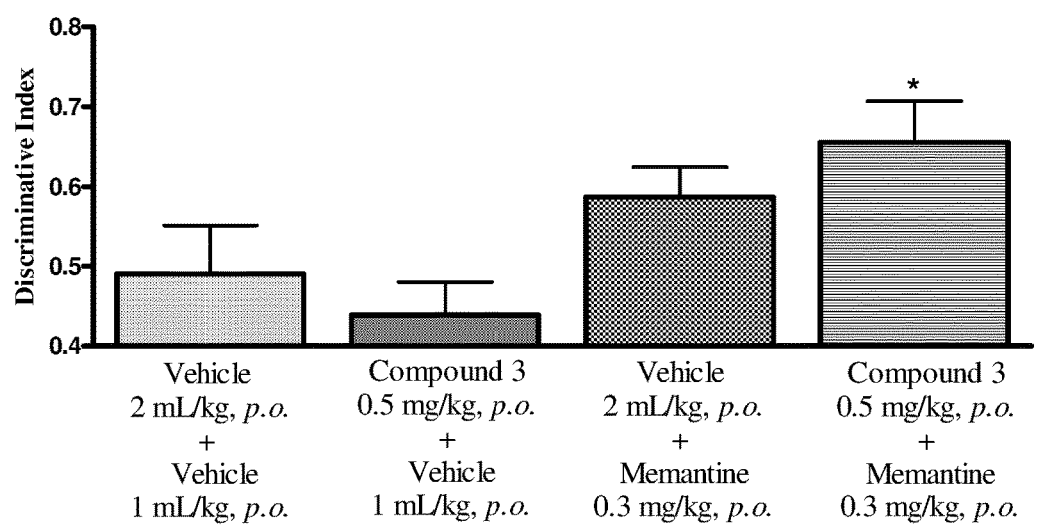
Figure 2:
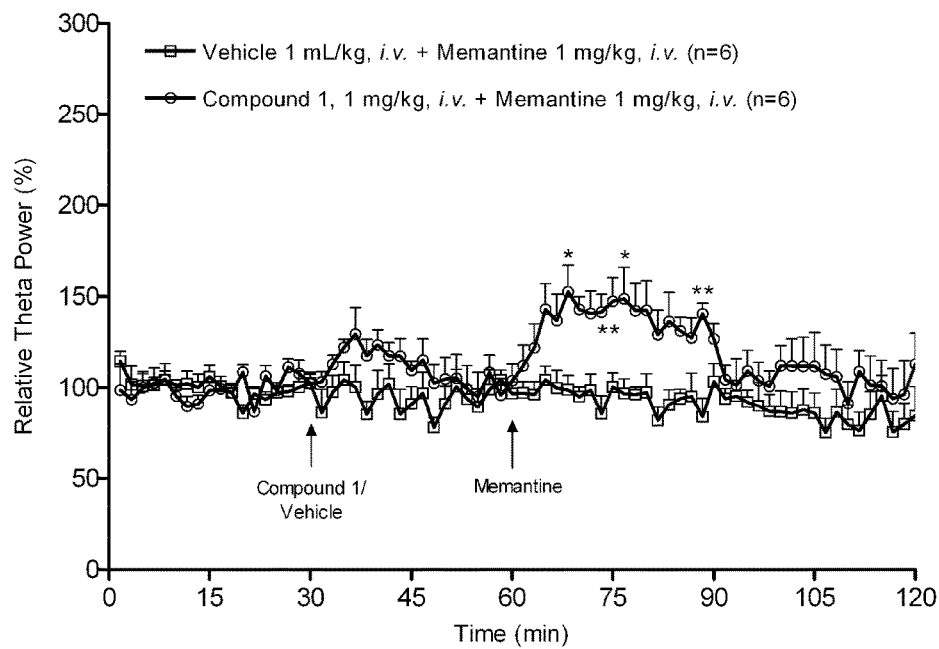
Figure 2:
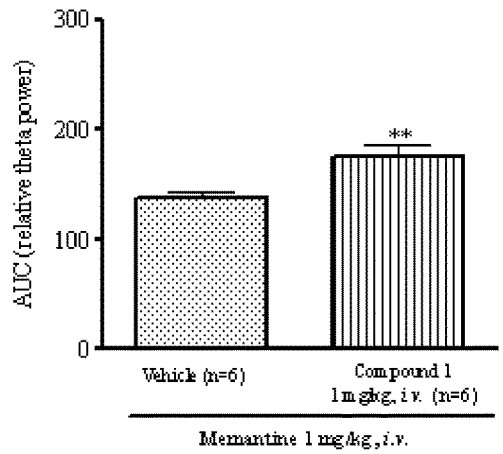
Figure 3:
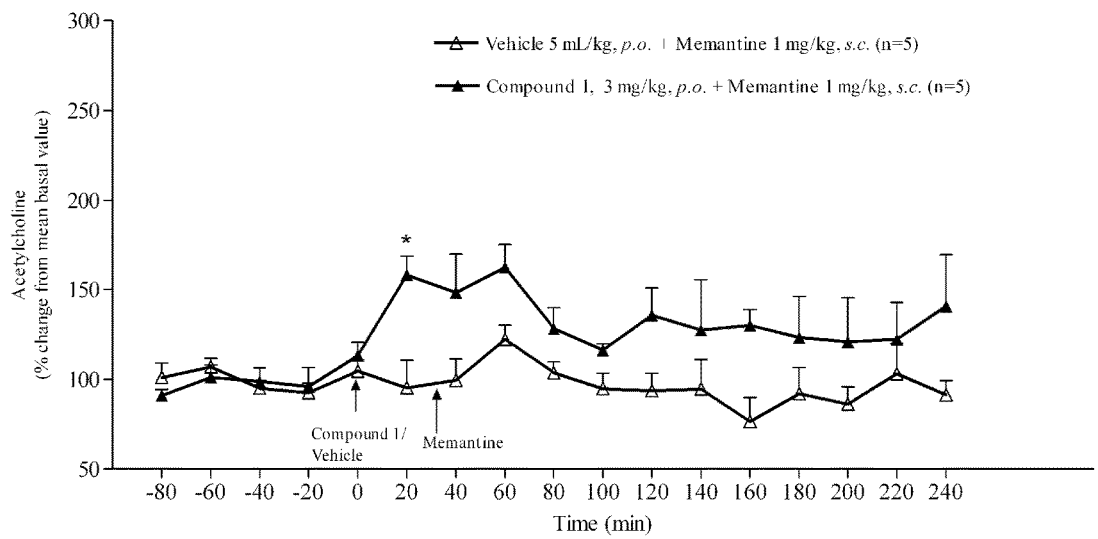
Figure 3:
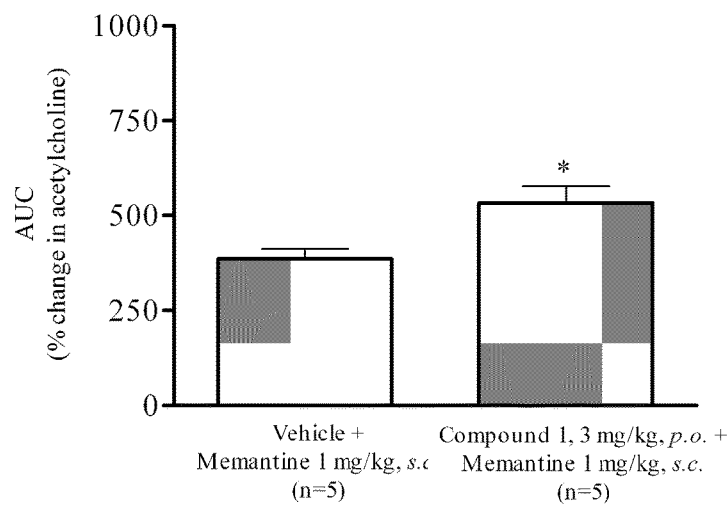

FIG. 1a depicts the results of the effect of co-treatment of compound 1 and memantine on cognition enhancing properties using object recognition task model FIG. 1b depicts the results of the effect of co-treatment of compound 2 and memantine on cognition enhancing properties using object recognition task model FIG. 1c depicts the results of the effect of a co-treatment of compound 3 and memantine on cognition enhancing properties using object recognition task model FIG. 2 depicts the effect of compound 1 and memantine combination on evoked theta modulation in dorsal hippocampus of anesthetized male Wistar rats FIG. 3 depicts the effect of compound 1 and memantine combination on extracellular levels of acetylcholine in ventral hippocampus of male Wistar rats

DETAILED DESCRIPTION

Unless otherwise stated, the following terms used in the specification and claims have the meanings given below:

The term, "5-HT$_6$ receptor antagonist" as used herein refers to a ligand or drug that has affinity towards 5-HT$_6$ receptor, blocks or inhibits the function/binding of agonist at the 5-HT$_6$ receptor.

The term, "pure 5-HT$_6$ receptor antagonist" as used herein refers to 5-HT$_6$ receptor antagonist which has very high selectivity (>250 fold) over closely related serotonin subtypes like 5-HT$_{1A}$, 5-HT$_{1B}$, 5-HT$_{1D}$, 5-HT$_{2A}$, 5-HT$_{2C}$, 5-HT$_4$, 5-HT$_{5A}$ and 5-HT$_7$.

Examples of the pure 5-HT$_6$ receptor antagonists include,
1-[(2-Bromophenyl)sulfonyl]-5-methoxy-3-[(4-methyl-1-piperazinyl)methyl]-1H-indole;
1-[(4-Fluorophenyl)sulfonyl]-5-methoxy-3-[(4-methyl-1-piperazinyl)methyl]-1H-indole; and
1-[(4-Isopropylphenyl)sulfonyl]-5-methoxy-3-[(4-methyl-1-piperazinyl)methyl]-1H-indole; or a pharmaceutically acceptable salt thereof.

Examples of pharmaceutically acceptable salt of the above identified compounds include but not limited to,
1-[(2-Bromophenyl)sulfonyl]-5-methoxy-3-[(4-methyl-1-piperazinyl)methyl]-1H-indole dimesylate monohydrate;
1-[(4-Fluorophenyl)sulfonyl]-5-methoxy-3-[(4-methyl-1-piperazinyl)methyl]-1H-indole dihydrochloride; and
1-[(4-Isopropylphenyl)sulfonyl]-5-methoxy-3-[(4-methyl-1-piperazinyl)methyl]-1H-indole dihydrochloride.

The term, "NMDA receptor antagonist" as used herein refers to class of compounds which act on glutamatergic system by inhibiting the NMDA receptor. Example of NMDA receptor antagonist is memantine. Memantine is a drug approved for treatment of moderate to severe dementia of the Alzheimer's disease. Memantine is NMDA receptor antagonist and sold under trade name Namenda® and Namenda XR® as hydrochloride salt.

The phrase, "therapeutically effective amount" is defined as an amount of a compound of the present invention that (i) treats the particular disease, condition or disorder, (ii) eliminates one or more symptoms of the particular disease, condition or disorder and (iii) delays the onset of one or more symptoms of the particular disease, condition or disorder described herein.

The term, "pharmaceutically acceptable salt" as used herein refers to salts of the active compound and are prepared by reaction with the appropriate acid or acid derivative, depending on the particular substituents found on the compounds described herein.

The term, "patient" as used herein refers to an animal. Preferably the term "patient" refers to mammal. The term mammal includes animals such as mice, rats, dogs, rabbits, pigs, monkeys, horses and human. More preferably the patient is human.

The term, "Alzheimer's disease" as used herein refers to a dementia that causes problems with memory, thinking and behavior. The Alzheimer's disease can be mild to severe.

The compound 1 as used herein is 1-[(2-Bromophenyl) sulfonyl]-5-methoxy-3-[(4-methyl-1-piperazinyl) methyl]-1H-indole dimesylate monohydrate which has the chemical structure,

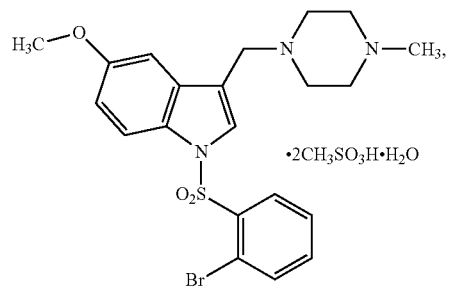

and the process for preparing this compound in large scale is described in WO2015083179A1.

The compound 2 as used herein is 1-[(4-Fluorophenyl) sulfonyl]-5-methoxy-3-[(4-methyl-1-piperazinyl)methyl]-1H-indole dihydrochloride which has the chemical structure,

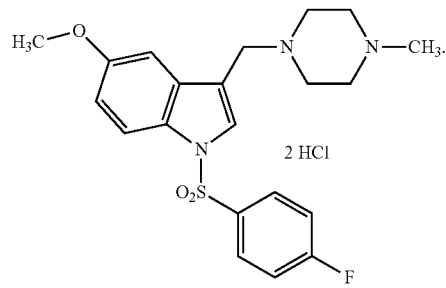 [SMILES: COc1ccc2c(c1)c(CN1CCN(C)CC1)cn2S(=O)(=O)c1ccc(F)cc1 ; "2 HCl"]

The compound 3 as used herein is 1-[(4-Isopropylphenyl) sulfonyl]-5-methoxy-3-[(4-methyl-1-piperazinyl)methyl]-1H-indole dihydrochloride which has the chemical structure,

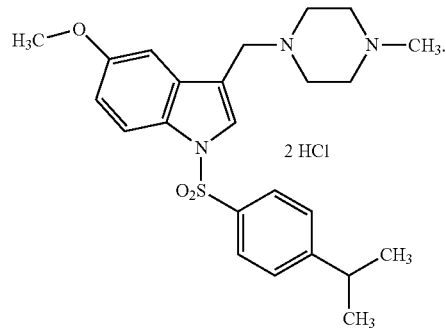 [SMILES: COc1ccc2c(c1)c(CN1CCN(C)CC1)cn2S(=O)(=O)c1ccc(C(C)C)cc1 ; "2 HCl"]

The term, "treatment' or 'treating" as used herein refers to any treatment of a disease in a mammal, including: (a) slowing or arresting the development of clinical symptoms; and/or (b) causing the regression of clinical symptoms.

The term, "compound for use" as used herein embrace any one or more of the following: (1) use of a compound, (2) method of use of a compound, (3) use in the treatment of, (4) the use for the manufacture of pharmaceutical composition/medicament for treatment/treating or (5) method of treatment/treating/preventing/reducing/inhibiting comprising administering an effective amount of the active compound to a subject in need thereof.

The term, "cognitive disorder" as used herein refers to a group of mental health disorders that principally affect learning, memory, perception, and problem solving, and include amnesia, dementia, and delirium. Cognitive disorders can result due to disease, disorder, ailment or toxicity. Example of cognitive disorders includes but not limited to Alzheimer's disease, schizophrenia, Parkinson's disease, lewy body dementia (LBD), vascular dementia and frontotemporal dementia (FTD). Preferably the cognitive disorder is Alzheimer's disease.

The term, "adjunct" or "adjunctive treatment" as used herein refers to an additional treatment to a patient who has already received at least one other therapy for cognitive disorder. A drug used as adjunctive therapy is administered to a patient to make that primary treatment works better.

EMBODIMENTS

The present invention encompasses all the combinations described herein without limitation, however, preferred aspects and elements of the invention are discussed herein in the form of the following embodiments.

In one embodiment, the present invention relates to combination of pure 5-HT$_6$ receptor antagonist and NMDA receptor antagonist; wherein the pure 5-HT$_6$ receptor antagonist is 1-[(2-Bromophenyl)sulfonyl]-5-methoxy-3-[(4-methyl-1-piperazinyl)methyl]-1H-indole dimesylate monohydrate.

In one embodiment, the present invention relates to combination of pure 5-HT$_6$ receptor antagonist and NMDA receptor antagonist; wherein the pure 5-HT$_6$ receptor antagonist is 1-[(4-Fluorophenyl)sulfonyl]-5-methoxy-3-[(4-methyl-1-piperazinyl)methyl]-1H-indole dihydrochloride.

In one embodiment, the present invention relates to combination of pure 5-HT$_6$ receptor antagonist and NMDA receptor antagonist; wherein the pure 5-HT$_6$ receptor antagonist is 1-[(4-Isopropylphenyl) sulfonyl]-5-methoxy-3-[(4-methyl-1piperazinyl)methyl]-1H-indole dihydrochloride.

In another embodiment, the present invention provides a combination of 1-[(2-Bromophenyl) sulfonyl]-5-methoxy-3-[(4-methyl-1-piperazinyl)methyl]-1H-indole or a pharmaceutically acceptable salt thereof and NMDA receptor antagonist or a pharmaceutically acceptable salt thereof which is more effective than the NMDA receptor antagonist or a pharmaceutically acceptable salt or 1-[(2-Bromophenyl) sulfonyl]-5-methoxy-3-[(4-methyl-1-piperazinyl)methyl]-1H-indole or a pharmaceutically acceptable salt alone.

In another embodiment, the present invention provides a combination of 1-[(2-Bromophenyl) sulfonyl]-5-methoxy-3-[(4-methyl-1-piperazinyl)methyl]-1H-indole dimesylate monohydrate and NMDA receptor antagonist or a pharmaceutically acceptable salt which is more effective than the NMDA receptor antagonist or a pharmaceutically acceptable salt or 1-[(2-Bromophenyl)sulfonyl]-5-methoxy-3-[(4-methyl-1-piperazinyl)methyl]-1H-indole dimesylate monohydrate alone.

In another embodiment, the present invention provides a combination of 1-[(4-Fluorophenyl)sulfonyl]-5-methoxy-3-[(4-methyl-1-piperazinyl)methyl]-1H-indole dihydrochloride and NMDA receptor antagonist or a pharmaceutically acceptable salt.

In another embodiment, the present invention provides a combination of 1-[(4-Isopropylphenyl) sulfonyl]-5-methoxy-3-[(4-methyl-1-piperazinyl)methyl]-1H-indole dihydrochloride and NMDA receptor antagonist or a pharmaceutically acceptable salt.

In yet another aspect, the present invention relates to combination of 1-[(4-Fluorophenyl)sulfonyl]-5-methoxy-3-[(4-methyl-1-piperazinyl)methyl]-1H-indole or a pharmaceutically acceptable salt thereof and memantine or a pharmaceutically acceptable salt thereof.

In yet another aspect, the present invention relates to combination of 1-[(4-Isopropylphenyl) sulfonyl]-5-methoxy-3-[(4-methyl-1-piperazinyl)methyl]-1H-indole or a pharmaceutically acceptable salt thereof and memantine or a pharmaceutically acceptable salt thereof.

In another embodiment, the present invention relates to the combination wherein the NMDA receptor antagonist is memantine hydrochloride.

In yet another embodiment, the present invention relates to the combination of 1-[(4-Fluorophenyl)sulfonyl]-5-methoxy-3-[(4-methyl-1-piperazinyl)methyl]-1H-indole dihydrochloride and memantine hydrochloride.

In yet another embodiment, the present invention relates to the combination of 1-[(4-Isopropylphenyl) sulfonyl]-5-methoxy-3-[(4-methyl-1-piperazinyl)methyl]-1H-indole dihydrochloride and memantine hydrochloride.

In another embodiment the pharmaceutically acceptable salt of the pure 5-HT$_6$ receptor antagonist includes but not limited to dimesylate monohydrate salt, dihydrochloride salt, oxalate salt, tartrate salt and the like. Preferably, the pharmaceutically acceptable salts are dimesylate monohydrate salt and dihydrochloride salt. More preferably, the pharmaceutically acceptable salt is dimesylate monohydrate salt.

In yet another aspect, the present invention relates a method of treating Alzheimer's disease comprising administering to a patient in need thereof a therapeutically effective amount of the said combination.

In yet another aspect, the present invention relates to the compound, 1-[(4-Fluorophenyl)sulfonyl]-5-methoxy-3-[(4-methyl-1-piperazinyl)methyl]-1H-indole or a pharmaceutically acceptable salt thereof for use in the adjunct treatment of cognitive disorders such as Alzheimer's disease, schizophrenia, Parkinson's disease, lewy body dementia, vascular dementia or frontotemporal dementia in a patient on treatment with NMDA receptor antagonist.

In yet another aspect, the present invention relates to the compound, 1-[(4-Isopropylphenyl)sulfonyl]-5-methoxy-3-[(4-methyl-1-piperazinyl)methyl]-1H-indole or a pharmaceutically acceptable salt thereof for use in the adjunct treatment of cognitive disorder such as Alzheimer's disease, schizophrenia, Parkinson's disease, lewy body dementia, vascular dementia or frontotemporal dementia in a patient on treatment with NMDA receptor antagonist.

In another embodiment, the present invention relates to a method of treating Alzheimer's disease comprising administering to a patient in need thereof a therapeutically effective amount of 1-[(2-Bromophenyl) sulfonyl]-5-methoxy-3-[(4-methyl-1-piperazinyl)methyl]-1H-indole or a pharmaceutically acceptable salt thereof in combination with NMDA receptor antagonist or a pharmaceutically acceptable salt thereof.

In another embodiment, the present invention relates to a method of treating Alzheimer's disease comprising administering to a patient in need thereof a therapeutically effective amount of 1-[(4-Fluorophenyl) sulfonyl]-5-methoxy-3-[(4-methyl-1-piperazinyl)methyl]-1H-indole or a pharmaceutically acceptable salt thereof in combination with NMDA receptor antagonist or a pharmaceutically acceptable salt thereof.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole or a pharmaceutically acceptable salt thereof in combination with NMDA receptor antagonist or a pharmaceutically acceptable salt thereof.

In another embodiment, the present invention relates to a method of treating Alzheimer's disease comprising administering to a patient in need thereof a therapeutically effective amount of 1-[(2-Bromophenyl) sulfonyl]-5-methoxy-3-[(4-methyl-1-piperazinyl)methyl]-1H-indole dimesylate monohydrate in combination with NMDA receptor antagonist or a pharmaceutically acceptable salt thereof.

In another embodiment, the present invention relates to a method of treating Alzheimer's disease comprising administering to a patient in need thereof a therapeutically effective amount of 1-[(4-Fluorophenyl) sulfonyl]-5-methoxy-3-[(4-methyl-1-piperazinyl)methyl]-1H-indole dihydrochloride in combination with NMDA receptor antagonist or a pharmaceutically acceptable salt thereof.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole dihydrochloride in combination with NMDA receptor antagonist or a pharmaceutically acceptable salt thereof.

In another embodiment, the present invention relates to a method of treating Alzheimer's disease comprising administering to a patient in need thereof a therapeutically effective amount of 1-[(2-Bromophenyl) sulfonyl]-5-methoxy-3-[(4-methyl-1-piperazinyl)methyl]-1H-indole dimesylate monohydrate in combination with memantine or a pharmaceutically acceptable salt thereof.

In another embodiment, the present invention relates to a method of treating Alzheimer's disease comprising administering to a patient in need thereof a therapeutically effective amount of 1-[(4-Fluorophenyl) sulfonyl]-5-methoxy-3-[(4-methyl-1-piperazinyl)methyl]-1H-indole dihydrochloride in combination with memantine or a pharmaceutically acceptable salt thereof.

In another embodiment, the present invention relates to a method of treating Alzheimer's disease comprising administering to a patient in need thereof a therapeutically effective amount of 1-[(4-Isopropylphenyl)sulfonyl]-5-methoxy-3-[(4-methyl-1-piperazinyl)methyl]-1H-indole dihydrochloride in combination with memantine or a pharmaceutically acceptable salt thereof.

In another embodiment, the present invention relates to method of treating Alzheimer's disease comprising administering to a patient in need thereof a therapeutically effective amount of 1-[(2-Bromophenyl) sulfonyl]-5-methoxy-3-[(4-methyl-1-piperazinyl)methyl]-1H-indole dimesylate monohydrate in combination with memantine hydrochloride.

In another embodiment, the present invention relates to method of treating Alzheimer's disease comprising administering to a patient in need thereof a therapeutically effective amount of 1-[(4-Fluorophenyl) sulfonyl]-5-methoxy-3-[(4-methyl-1-piperazinyl)methyl]-1H-indole dihydrochloride in combination with memantine hydrochloride.

In another embodiment, the present invention relates to a method of treating Alzheimer's disease comprising administering to a patient in need thereof a therapeutically effective amount of 1-[(4-Isopropylphenyl) sulfonyl]-5-methoxy-3-[(4-methyl-1-piperazinyl)methyl]-1H-indole dihydrochloride in combination with memantine hydrochloride.

In another embodiment, the present invention relates to 1-[(2-Bromophenyl) sulfonyl]-5-methoxy-3-[(4-methyl-1-piperazinyl)methyl]-1H-indole dimesylate monohydrate for use in the treatment of Alzheimer's disease in combination with memantine or a pharmaceutically acceptable salt thereof.

In another embodiment, the present invention relates to 1-[(4-Fluorophenyl) sulfonyl]-5-methoxy-3-[(4-methyl-1-piperazinyl)methyl]-1H-indole dihydrochloride for use in the treatment of Alzheimer's disease in combination with memantine or a pharmaceutically acceptable salt thereof.

In another embodiment, the present invention relates to 1-[(4-Isopropylphenyl) sulfonyl]-5-methoxy-3-[(4-methyl-1-piperazinyl)methyl]-1H-indole dihydrochloride for use in the treatment of Alzheimer's disease in combination with memantine or a pharmaceutically acceptable salt thereof.

In another embodiment, the present invention relates to 1-[(2-Bromophenyl) sulfonyl]-5-methoxy-3-[(4-methyl-1-piperazinyl)methyl]-1H-indole dimesylate monohydrate for use in the treatment of Alzheimer's disease in combination with memantine hydrochloride.

In another embodiment, the present invention relates to 1-[(4-Fluorophenyl) sulfonyl]-5-methoxy-3-[(4-methyl-1-piperazinyl)methyl]-1H-indole dihydrochloride for use in the treatment of Alzheimer's disease in combination with memantine hydrochloride.

In another embodiment, the present invention relates to 1-[(4-Isopropylphenyl) sulfonyl]-5-methoxy-3-[(4-methyl-1-piperazinyl)methyl]-1H-indole dihydrochloride for use in the treatment of Alzheimer's disease in combination with memantine hydrochloride.

In another embodiment, the present invention relates to use of 1-[(2-Bromophenyl) sulfonyl]-5-methoxy-3-[(4-methyl-1-piperazinyl)methyl]-1H-indole or a pharmaceutically acceptable salt in the manufacture of a medicament for treatment of Alzheimer's disease in combination with memantine or a pharmaceutically acceptable salt thereof.

In another embodiment, the present invention relates to use of 1-[(4-Fluorophenyl)sulfonyl]-5-methoxy-3-[(4-methyl-1-piperazinyl)methyl]-1H-indole or a pharmaceutically acceptable salt thereof in the manufacture of a medicament for treatment of Alzheimer's disease in combination with memantine or a pharmaceutically acceptable salt thereof.

In another embodiment, the present invention relates to use of 1-[(4-Isopropylphenyl) sulfonyl]-5-methoxy-3-[(4-methyl-1-piperazinyl)methyl]-1H-indole or a pharmaceutically acceptable salt thereof in the manufacture of a medicament for treatment of Alzheimer's disease in combination with memantine or a pharmaceutically acceptable salt thereof.

In another embodiment, the present invention relates to use of 1-[(2-Bromophenyl) sulfonyl]-5-methoxy-3-[(4-methyl-1-piperazinyl)methyl]-1H-indole or a pharmaceutically acceptable salt in the manufacture of a medicament for treatment of Alzheimer's disease in combination with memantine hydrochloride.

In another embodiment, the present invention relates to use of 1-[(4-Fluorophenyl)sulfonyl]-5-methoxy-3-[(4-methyl-1-piperazinyl)methyl]-1H-indole or a pharmaceutically acceptable salt in the manufacture of a medicament for treatment of Alzheimer's disease in combination with memantine hydrochloride.

In another embodiment, the present invention relates to use of 1-[(4-Isopropylphenyl) sulfonyl]-5-methoxy-3-[(4-methyl-1-piperazinyl)methyl]-1H-indole or a pharmaceutically acceptable salt in the manufacture of a medicament for treatment of Alzheimer's disease in combination with memantine hydrochloride.

In another embodiment, the present invention relates to use of 1-[(2-Bromophenyl) sulfonyl]-5-methoxy-3-[(4-methyl-1-piperazinyl)methyl]-1H-indole dimesylate monohydrate in the manufacture of a medicament for treatment of Alzheimer's disease in combination with memantine hydrochloride.

In another embodiment, the present invention relates to use of 1-[(4-Fluorophenyl)sulfonyl]-5-methoxy-3-[(4-methyl-1-piperazinyl)methyl]-1H-indole dihydrochloride in the manufacture of a medicament for treatment of Alzheimer's disease in combination with memantine hydrochloride.

In another embodiment, the present invention relates to use of 1-[(4-Isopropylphenyl) sulfonyl]-5-methoxy-3-[(4-methyl-1-piperazinyl)methyl]-1H-indole dihydrochloride in the manufacture of a medicament for treatment of Alzheimer's disease in combination with memantine hydrochloride.

In another embodiment, the present invention relates to the combination for the treatment of Alzheimer's disease; wherein the Alzheimer's disease is mild Alzheimer's disease.

In another embodiment, the present invention relates to the combination for the treatment of Alzheimer's disease; wherein the Alzheimer's disease is moderate Alzheimer's disease.

In another embodiment, the present invention relates to the combination for the treatment of Alzheimer's disease; wherein the Alzheimer's disease is severe Alzheimer's disease.

In another embodiment, the present invention relates to the said combination wherein the active ingredients can be administered to a patient concurrently or separately.

In yet another aspect, the active ingredients of the combination of the present invention are normally administered by formulating the active ingredients into a pharmaceutical composition in accordance with standard pharmaceutical practice.

In yet another aspect, the active ingredients of the said combination of the present invention may be administered in all possible routes of administration.

In yet another aspect, the active ingredients of the combination of the present invention may be administered by oral, nasal, local, dermal or parenteral routes.

In yet another aspect, the active ingredients of the combination of the present invention can be administered by the same or different route of administration. For instance, the 5-HT$_6$ receptor antagonist of the instant invention can be administered orally and the NMDA receptor antagonist can be administered transdermally.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, co-solvents, preservatives, wetting agents, thickening agents, antifoaming agents, sweetening agents, flavouring agents, antioxidants, colorants, solubulizers, plasticizer, dispersing agents and the like. Excipients are selected from microcrystalline cellulose, mannitol, lactose, pre-gelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

In yet another aspect, the pharmaceutical composition of the combination of the instant invention can be conventional formulations such as immediate release formulations, modified release formulations such as sustained release formulations, delayed release formulations and extended release formulations or new delivery systems such as oral disintegrating formulations and transdermal patches.

The dose of the active compounds can vary depending on factors such as age and weight of patient, nature, route of administration and severity of the disease to be treated and such other factors. Therefore, any reference regarding pharmacologically effective amount of the compounds 1, 2 and 3 refers to the aforementioned factors.

In yet another aspect, the 5-HT$_6$ receptor antagonist can be co-administered with NMDA receptor antagonist at a daily dose of 1 mg to 300 mg; such as 1, 5, 10, 20, 25, 30, 50, 75, 100, 150, 200 or 300 mg, preferably at a daily dose of 10, 25, 30, 50, 75, 100 or 150 mg and most preferably at a daily dose of 10, 25, 50, 75, 100 or 125 mg.

In yet another aspect, the memantine can be co-administered with 5-HT$_6$ receptor antagonist at a daily dose of 1 mg to 40 mg; such as 5, 10, 14, 20, 28 or 40 mg, preferably at a daily dose of 5, 10, 14, 20 or 28 mg and most preferably at a daily dose of 5, 7, 10, 14, 20 or 28 mg.

In yet another aspect, the treatment comprises administering to the patient 1 mg to 200 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 1 mg to 10 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 25 mg to 125 mg of 1-[(2-Bromophenyl) sulfonyl]-5-methoxy-3-[(4-methyl-1-piperazinyl)methyl]-1H-indole or a pharmaceutically acceptable salt thereof, per day.

In yet another aspect, the treatment comprises administering to the patient 150 mg to 200 mg of 1-[(2-Bromophenyl)sulfonyl]-5-methoxy-3-[(4-methyl-1-piperazinyl) methyl]-1H-indole or a pharmaceutically acceptable salt thereof, per day.

In yet another aspect, the treatment comprises administering to the patient 10 mg to 100 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 10 mg to 50 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 25 mg to 50 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 75 mg to 100 mg of 1-[(2-Bromophenyl)sulfonyl]-5-methoxy-3-[(4-methyl-1-piperazinyl)methyl]-1H-indole or a pharmaceutically acceptable salt thereof, per day.

In yet another aspect, the treatment comprises administering to the patient 1 mg to 30 mg of memantine or a pharmaceutically acceptable salt thereof, per day.

In yet another aspect, the treatment comprises administering to the patient 5 mg to 25 mg of memantine or a pharmaceutically acceptable salt thereof, per day.

In yet another aspect, the treatment comprises administering to the patient 5 mg, 10 mg, 25 mg or 30 mg of memantine or a pharmaceutically acceptable salt thereof, per day.

In yet another aspect, the treatment comprises administering the active compounds to the patient one to three times per day, one to three times per week or one to three times per month. Preferably, the treatment comprises administering the compound to a patient once a day, twice a day, or thrice a day. More preferably, the treatment comprises administering the compound to a patient once a day.

The examples given below are provided by the way of illustration only and therefore should not be construed to limit the scope of the invention.

Abbreviations:

| | |
|---|---|
| 5-HT$_{1A}$ | 5-Hydroxytryptamine 1A receptor |
| 5-HT$_{1B}$ | 5-Hydroxytryptamine 1B receptor |
| 5-HT$_{1D}$ | 5-Hydroxytryptamine 1D receptor |
| 5-HT$_{2A}$ | 5-Hydroxytryptamine 2A receptor |
| 5-HT$_{2C}$ | 5-Hydroxytryptamine 2C receptor |
| 5-HT$_4$ | 5-Hydroxytryptamine 4 receptor |
| 5-HT$_{5A}$ | 5-Hydroxytryptamine 5A receptor |
| 5-HT$_6$ | 5-Hydroxytryptamine 6 receptor |
| 5-HT$_7$ | 5-Hydroxytryptamine 7 receptor |
| ANOVA | Analysis of variance |
| AP | Anterior Posterior |
| aCSF | Artificial Cerebrospinal fluid |
| cAMP | Cyclic adenosine monophosphate |
| CaCl$_2$•2H$_2$O | Calcium Chloride dihydrate |
| DV | Dorsal Ventral |
| EC$_{50}$ | Half maximal effective concentration |
| EDTA | Ethylenediaminetetraacetic acid |
| EEG | Electronencephalogram |
| GPCR | G-Protein Coupled Receptor |
| HCl | Hydrochloric acid |
| h | Hour (s) |

-continued

Abbreviations:

| | |
|---|---|
| i.p | Intraperitoneal |
| i.v. | Intravenous |
| KCl | Potassium chloride |
| K$_b$ | Binding constant |
| K$_i$ | Inhibitory constant |
| LC-MS/MS | Liquid chromatography-Mass spectrometry/Mass spectrometry |
| mg | Milligram |
| MgCl$_2$ | Magnesium chloride |
| min | Minute (s) |
| ML | Medial Lateral |
| mM | Millimolar |
| NaCl | Sodium chloride |
| NaH$_2$PO$_4$•2H$_2$O | Sodium dihydrogen phosphate dihydrate |
| Na$_2$HPO$_4$•7H$_2$O | Sodium monohydrogen phosphate heptahydrate |
| nM | Nanomolar |
| nmol/L | Nanomoles per litre |
| NPO | Nucleus Pontis Oralis |
| p.o. | Per oral |
| µM | Micromolar |
| s.c. | Subcutaneous |
| S.E.M. | Standard error of the mean |
| θ | Theta |

Example 1

Determination of K$_b$ Values at 5-HT$_6$ Receptor:

A stable CHO cell line expressing recombinant human 5-HT$_6$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compound were added along with 10 µM of serotonin in OptiMEM medium to the cells. The incubation was continued at 37° C. in CO$_2$ incubator for 4 hours. Medium was removed and cells were washed with phosphate buffered saline. The cells were lysed and luciferase activity was measured in a Luminometer. Luminescence units were plotted against the compound concentrations using Graphpad software. EC$_{50}$ values of the compounds were defined as the concentration required in reducing the luciferase activity by 50%. The K$_b$ values were calculated by feeding the concentration of agonist used in the assay and its EC$_{50}$ value in the same software.

References: *Molecular Brain Research*, 2001, 90, 110-117 and *British Journal of Pharmacology*, 2006, 148, 1133-1143.

Results:

Compounds 1, 2 and 3 exhibit antagonistic activity in CRE-Luc based reporter gene assay on human recombinant 5-HT$_6$ receptor with no detectable agonist activity. The K$_b$ values tabulated below are average of three independent experiments.

| S. No | Example | K$_b$ (nM) |
|---|---|---|
| 1 | Compound 1 | 4.2 ± 0.9 |
| 2 | Compound 2 | 7.2 ± 1.8 |
| 3 | Compound 3 | 1.6 ± 0.3 |

Example 2

Determination of $K_i$ Value at 5-HT$_6$ Receptor

Compound was tested at MDS pharma services and Novascreen according to the following procedures.

Materials and Methods:

Receptor source: Human recombinant expressed in Hela cells

Radioligand: [$^3$H]-LSD (60-80 Ci/mmol)

Final ligand concentration—[1.5 nM]

Non-Specific Ligand: 5 µM Serotonin (5-HT)

Reference compound: Methiothepin mesylate

Positive control: Methiothepin mesylate

Incubation conditions: Reactions were carried out in 50 mM Tris-HCl (pH 7.4) containing 10 mM MgCl$_2$, 0.5 mM EDTA for 60 minutes at 37° C. The reaction was terminated by rapid vacuum filtration onto the glass fiber filters. Radioactivity trapped onto the filters was determined and compared to the control values in order to ascertain any interactions of the test compound(s) with the cloned serotonin 5-HT$_6$ binding site.

Reference: *Molecular Pharmacology*, 1993, 43, 320-327.

Results:

Compounds 1, 2 and 3 selectively bind to 5-HT$_6$ receptor when tested by the in-vitro radioligand binding technique on human recombinant 5-HT$_6$ receptor. The $K_i$ values are tabulated below.

| S. No | Example | $K_i$ (nM) |
| --- | --- | --- |
| 1 | Compound 1 | 2.04 |
| 2 | Compound 2 | 4.96 |
| 3 | Compound 3 | 3.67 |

Example 3

Determination of $K_i$ Value at 5-HT$_{2A}$ Receptor

Compound was tested according to the following procedures.

Materials and Methods:

Receptor source: Recombinant mammalian cells

Radioligand: [$^3$H]-Ketanserine (47.3 Ci/mmol)

Final ligand concentration—[1.75 nM]

Non-Specific Ligand: 0.1 mM 1-Naphthylpiperazine (1-NP)

Reference compound: 1-Naphthylpiperazine (1-NP)

Positive control: 1-Naphthylpiperazine (1-NP)

Incubation conditions: Reactions were carried out in 67 mM Tris-HCl (pH 7.4) for 4 hours at 37° C. The reaction was terminated by rapid vacuum filtration onto the glass fiber filters. Radioactivity trapped onto the filters was determined and compared to the control values in order to ascertain any interactions of the test compound(s) with the cloned serotonin 5-HT$_{2A}$ binding site.

Reference: *Methods in Molecular Biology*, 2002, 190, 31-49

Results:

Compounds 1, 2 and 3 bind weakly to 5-HT$_{2A}$ receptor when tested by the in-vitro radioligand binding technique on human recombinant 5-HT$_{2A}$ receptor. The Ki values tabulated below are average of three independent experiments.

| S. No | Example | $K_i$ |
| --- | --- | --- |
| 1 | Compound 1 | 2514 ± 377 nM |
| 2 | Compound 2 | >10 µM |
| 3 | Compound 3 | 926 ± 317 nM |

Example 4

Test compounds were also evaluated for their 5-HT$_6$ receptor selectivity over closely related serotonin subtypes like 5-HT$_{1A}$, 5-HT$_{1B}$, 5-HT$_{1D}$, 5-HT$_{2B}$, 5-HT$_{2C}$, 5-HT$_4$, 5-HT$_{5A}$, and 5-HT$_7$ in commercial panel at Novascreen.

Compounds 1, 2 and 3 have shown selectivity of more than 250-fold over these receptor subtypes.

Example 5

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) in the absence of any objects on day 1.

Rats received vehicle or test compounds or memantine or test compound and memantine, before familiar (T$_1$) and choice (T$_2$) trials. During the familiarization phase (T$_1$), the rats were placed individually in the arena for 3 minutes, in which two identical objects (a$_1$ and a$_2$) were positioned 10 cm from the wall. 24 hours after T$_1$, trial for long-term memory test was assessed. The same rats were placed in the same arena as they were placed during T$_1$ trial. During the choice phase (T$_2$) rats were allowed to explore the arena for 3 minutes in presence of a copy of familiar object (a$_3$) and one novel object (b). During the T$_1$ and T$_2$ trial, explorations of each object (defined as sniffing, licking, chewing or having moving vibrissae whilst directing the nose towards the object at a distance of less than 1 cm) were recorded using stopwatch.

T$_1$ is the total time spent exploring the familiar objects (a1+a2).

T$_2$ is the total time spent exploring the familiar object and novel object (a3+b).

Discriminative index is ratio of time spent exploring the novel object divided by sum of time spent exploring the novel object and familiar object in choice trial (T$_2$).

The object recognition test was performed as described in *Behavioural Brain Research*, 1988, 31, 47-59.

Results:

No significant increase in discriminative index was observed in the group treated with memantine when compared to the vehicle treatment. However the group co-treated with test compounds and memantine showed significant improvement in the memory end point (discriminative index). The results of this study are provided in FIGS. 1a, 1b & 1c.

Example 6

Evaluation of Theta Modulation in Dorsal Hippocampus of Anesthetized Male Wistar Rats Synchronous hippocampal EEG activity occurring in a θ rhythm (frequency range of 4 to 8 Hz) has been associated with mnemonic processes in vivo.

Experimental Procedure

Male Wistar rats (240-320 g) were anesthetized with 1.2 to 1.5 g/kg urethane intraperitoneally, under anesthesia a catheter was surgically implanted in the left femoral vein for administration of drugs. After cannulation, the animal was placed in a stereotaxic frame for implanting an electrode (stainless steel wire, Plastics One) into the dorsal hippocampus (AP, −3.8 mm; ML, +2.2 mm; DV, −1.5 mm from dura; Paxinos and Watson, 1994) and bipolar stimulating electrode (untwisted stainless steel wires, separated by 0.75-1.0 mm at their tips, Plastics One) was implanted in the Nucleus Pontis Oralis (NPO), (AP, −7.8 mm; ML, ±1.8 mm; DV, −6.0 mm; Paxinos and Watson, 1994). Additionally one electrode was implanted into the cerebellum which served as a reference. Hippocampal θ rhythm was evoked via a 6-s electrical stimulation train (20-160 μA, 0.3-ms pulse duration, 250 Hz) delivered to the NPO at a rate of 0.01 trains/s with a Grass S88 stimulator and PSIU6 stimulus isolation unit (Grass Medical Instruments, Quincy, Mass.). EEG was recorded at a rate of 1000 Hz using Ponemah (Version 5.2) software and stored for off-line analysis using NeuroScore (Version 3.0). Baseline amplitude level was achieved using the current required to elicit θ rhythm to 50% of the maximal amplitude under control conditions. After the stabilization period of one hour, Baseline recording was done for 30 min followed by the treatment of vehicle or compound 1 (1 mg/kg, i.v.). Memantine (1 mg/kg, i.v.) was administered 30-min after vehicle or compound 1 treatment and recording was continued for additional 1 hour.

Power in the θ rhythm frequency in the stimulation period during the 30 min baseline period was calculated and the percent changes in these measures post treatment were calculated. The percent change in relative theta power after combination treatment of compound 1 and memantine was compared with memantine alone using two-way analysis of variance (time and treatment), followed by Bonferroni's posttests test. Statistical significance was considered at a p value less than 0.05.

Reference: Paxinos G. and Watson C. (2004) Rat brain in stereotaxic coordinates. Academic Press, New York Results:

Treatment with memantine (1 mg/kg, i.v.) alone produced no change in hippocampal theta power. Compound 1 (1 mg/kg, i.v.) in combination with memantine (1 mg/kg, i.v.) produced significant increase in theta power levels and peak levels reached up to 153±15% of pre-dose levels (FIG. 2).

Example 7

Evaluation of Acetylcholine Modulation in Ventral Hippocampus of Male Wistar Rats Experimental Procedure:

Male Wistar rats (240-300 g body weight) were stereotaxically implanted with a microdialysis guide cannula in ventral hippocampus (AP: −5.2 mm, ML: +5.0 mm, DV: −3.8 mm) under isoflurane anesthesia. Co-ordinates were taken according to atlas for the rat brain (Paxinos and Watson 2004) with reference points taken from bregma and vertical from the skull. The rats were allowed to recover individually for four-five days in a round bottom Plexiglas bowl with free access to feed and water.

After surgical recovery of 4-5 days, male Wistar rats were connected to dual quartz lined two-channel liquid swivel (Instech, UK) on a counter balance lever arm, which allowed unrestricted movements of the animal. Sixteen hours before start of study, a pre-equilibrated microdialysis probe (4 mm dialysis membrane) was inserted into the ventral hippocampus through the guide cannula. On the day of study, probe was perfused with artificial cerebrospinal fluid (aCSF; NaCl 147 mM, KCl 3 mM, $MgCl_2$ 1 mM, $CaCl_2.2H_2O$ 1.3 mM, $NaH_2PO_4.2H_2O$ 0.2 mM and $Na_2HPO_4.7H_2O$ 1 mM, pH 7.2) at a flow rate of 1.5 μL/min and a stabilization period of 2 h was maintained. Five basal samples were collected at 20 min intervals prior to the treatment of compound 1 (3 mg/kg, p.o.) or vehicle. Memantine (1 mg/kg, s.c.) was administered 30 min after administration of compound 1. Dialysate samples were collected for an additional period of 4 h post treatment of compound 1. Dialysates were stored below −50° C. prior to analysis.

Acetylcholine in dialysate was quantified using LC-MS/MS method in the calibration range of 0.099 nmol/L-70.171 nmol/L.

All microdialysis data for acetylcholine was plotted as percent change from mean dialysate basal concentrations with 100% defined as the average of five pre-dose values. The percent change in acetylcholine levels were compared with memantine using two-way analysis of variance (time and treatment), followed by Bonferroni's posttest. Area under the curve (AUC) values for percent change in acetylcholine levels were calculated and the statistical significance between the mean AUC value were compared against memantine treatment using one-way ANOVA followed by Dunnett's test. Statistical significance was considered at a p value less than 0.05. Incorrect probe placement was considered as criteria to reject the data from animal.

Reference: Paxinos G. and Watson C. (2004) Rat brain in stereotaxic coordinates. Academic Press, New York Results:

Treatment with memantine (1 mg/kg, s.c.) alone produced moderate change in hippocampal acetylcholine levels; the increase in acetylcholine after combination of compound 1 (3 mg/kg, p.o.) and memantine (1 mg/kg, s.c.) was significantly higher compared to memantine alone with mean maximum increase of 162±13% from pre-dose levels (FIG. 3 (a)).

Mean area under the curve values (AUC) calculated after compound 1 (1 mg/kg, p.o.) and memantine (1 mg/kg, s.c.) combined treatment were significantly higher compared to memantine (1 mg/kg, s.c.) alone (FIG. 3b)).

We claim:

1. A synergistic combination comprising pure 5-HT6 receptor antagonist and NMDA receptor antagonist as the only active agents, wherein the pure 5-HT6 receptor antagonist is selected from, 1-[(2-Bromophenyl)sulfonyl]-5-methoxy-3-[(4-methyl-1-piperazinyl)methyl]-1H-indole or a pharmaceutically acceptable salt thereof, wherein the NMDA receptor antagonist is memantine or a pharmaceutically acceptable salt thereof and wherein the 5-HT6 receptor antagonist or its pharmaceutically acceptable salt is in an amount of 1 mg to 300 mg.

2. The combination as claimed in claim 1, wherein the pharmaceutically acceptable salt of the pure 5-HT6 receptor antagonist is 1-[(2-Bromophenyl)sulfonyl]-5-methoxy-3-[(4-methyl-1-piperazinyl)methyl]-1H-indole dimesylate monohydrate.

3. The combination as claimed in claim 1, wherein the pharmaceutically acceptable salt of memantine is memantine hydrochloride.

4. The combination as claimed in claim 1, wherein said pure 5-HT6 receptor antagonist is 1-[(2-Bromophenyl)sulfonyl]-5-methoxy-3-[(4-methyl-1-piperazinyl)methyl]-1H-indole dimesylate monohydrate and said NMDA receptor antagonist is memantine hydrochloride.

5. The combination as claimed in claim 1, is for the treatment of a cognitive disorder in a patient, wherein the cognitive disorder is selected from Alzheimer's disease.

6. A method of treatment of a cognitive disorder comprising the step of administering to a patient in need thereof a therapeutically effective amount of the combination as claimed in claim 1 wherein the cognitive disorder is Alzheimer's disease.

7. A method of treating Alzheimer's disease in a patient comprising the step of administering to said patient a synergistic combination of 1-[(2-Bromophenyl)sulfonyl]-5-methoxy-3-[(4-methyl-1-piperazinyl)methyl]-1H-indole or a pharmaceutically acceptable salt thereof, memantine or a pharmaceutically acceptable salt thereof as the only active agents and wherein the 5-HT6 receptor antagonist or its pharmaceutically acceptable salt is in an amount of 1 mg to 300 mg.

8. The method as claimed in claim 7, wherein the pharmaceutically acceptable salt of 1-[(2-Bromophenyl)sulfonyl]-5-methoxy-3-[(4-methyl-1-piperazinyl)methyl]-1H-indole is 1-[(2-Bromophenyl)sulfonyl]-5-methoxy-3-[(4-methyl-1-piperazinyl)methyl]-1H-indole dimesylate monohydrate.

9. The method of treating Alzheimer's disease as claimed in claim 7, wherein the patient is administered 1 mg to 200 mg of 1-[(2-Bromophenyl)sulfonyl]-5-methoxy-3-[(4-methyl-1-piperazinyl)methyl]-1H-indole or a pharmaceutically acceptable salt thereof per day.

10. The method of treating Alzheimer's disease as claimed in claim 7, wherein the patient is administered 1 mg to 10 mg of 1-[(2-Bromophenyl)sulfonyl]-5-methoxy-3-[(4-methyl-1-piperazinyl)methyl]-1H-indole or a pharmaceutically acceptable salt thereof per day.

11. The method of treating Alzheimer's disease as claimed in claim 7, wherein the patient is administered 25 mg to 125 mg of 1-[(2-bromophenyl)sulfonyl]-5-methoxy-3-[(4-methyl-1-piperazinyl)methyl]-1H-indole or a pharmaceutically acceptable salt thereof per day.

12. The method of treating Alzheimer's disease as claimed in claim 7, wherein the patient is administered 150 mg to 200 mg of 1-[(2-Bromophenyl)sulfonyl]-5-methoxy-3-[(4-methyl-1-piperazinyl)methyl]-1H-indole or a pharmaceutically acceptable salt thereof per day.

13. The method of treating Alzheimer's disease as claimed in claim 7, wherein the patient is administered 25 mg to 75 mg of 1-[(2-Bromophenyl)sulfonyl]-5-methoxy-3-[(4-methyl-1-piperazinyl)methyl]-1H-indole or a pharmaceutically acceptable salt thereof per day.

14. The method of treating Alzheimer's disease as claimed in claim 7, wherein the patient is administered 75 mg to 150 mg of 1-[(2-Bromophenyl)sulfonyl]-5-methoxy-3-[(4-methyl-1-piperazinyl)methyl]-1H-indole or a pharmaceutically acceptable salt thereof per day.

15. The method of treating Alzheimer's disease as claimed in claim 7, wherein the patient is administered 1 mg to 40 mg of memantine or a pharmaceutically acceptable salt thereof per day.

16. The method of treating Alzheimer's disease as claimed in claim 7, wherein the patient is administered 5 mg to 28 mg memantine or a pharmaceutically acceptable salt thereof per day.

17. A pharmaceutical composition comprising the combination of pure 5-HT6 receptor antagonist and the NMDA receptor antagonist as claimed in claim 1, and pharmaceutically acceptable excipients.

18. The pharmaceutical composition as claimed in claim 17, for treatment of cognitive disorder selected from Alzheimer's disease.

19. The pharmaceutical composition as claimed in claim 17, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 35 mg to 200 mg.

20. The pharmaceutical composition as claimed in claim 17, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 200 mg to 300 mg.

21. The pharmaceutical composition as claimed in claim 17, wherein the 1-[(2-Bromophenyl)sulfonyl]-5-methoxy-3-[(4-methyl-1-piperazinyl)methyl]-1H-indole or a pharmaceutically acceptable salt thereof is present in an amount of 75 mg or 125 mg.

22. The pharmaceutical composition as claimed in claim 17, wherein the memantine or a pharmaceutically acceptable salt thereof is present in an amount of 5 mg to 40 mg.

23. The method of treating Alzheimer's disease as claimed in claim 7, wherein the 1-[(2-Bromophenyl)sulfonyl]-5-methoxy-3-[(4-methyl-1-piperazinyl)methyl]-1H-indole or a pharmaceutically acceptable salt thereof is administered to the patient by oral, nasal, local, dermal or parenteral routes.

24. The method of treating Alzheimer's disease as claimed in claim 7, wherein the 1-[(2-bromophenyl)sulfonyl]-5-methoxy-3-[(4-methyl-1-piperazinyl)methyl]-1H-indole or a pharmaceutically acceptable salt thereof is administered to the patient one to three times per day, one to three times per week or one to three times per month.

* * * * *